(12) United States Patent
Cascone

(10) Patent No.: US 7,279,054 B2
(45) Date of Patent: Oct. 9, 2007

(54) DENTAL PROSTHESIS METHOD AND ALLOYS

(75) Inventor: Paul J. Cascone, Del Mar, CA (US)

(73) Assignee: The Argen Corporation, San Diego, CA (US)

( * ) Notice: Subject to any disclaimer, the term of this patent is extended or adjusted under 35 U.S.C. 154(b) by 1 day.

(21) Appl. No.: 10/846,314

(22) Filed: May 14, 2004

(65) Prior Publication Data

US 2005/0252339 A1    Nov. 17, 2005

(51) Int. Cl.
C22C 5/02    (2006.01)
(52) U.S. Cl. ...................... 148/430; 420/507
(58) Field of Classification Search ................ 148/430; 420/507–512
See application file for complete search history.

(56) References Cited

U.S. PATENT DOCUMENTS

| 5,853,661 A | 12/1998 | Fischer |
| 5,922,276 A | 7/1999 | Cascone |
| 2004/0032594 A1 | 2/2004 | Weber et al. |

FOREIGN PATENT DOCUMENTS

| DE | 44 39 793 C1 | 10/1995 |
| EP | 0717118 B8 | 6/1996 |
| EP | 0 729 740 A2 | 9/1996 |
| EP | 0 729 740 A3 | 3/2000 |
| JP | 56003636 A * | 1/1981 |
| JP | 07166266 A * | 6/1995 |
| WO | WO97/28779 | 8/1997 |
| WO | WO 01/55465 A1 | 8/2001 |
| WO | WO 2004/101835 A1 | 11/2004 |

OTHER PUBLICATIONS

Internet Documents(2): Shosuke, Otsuka, et al.; Japan Abstract JP9067628A2; "*Dental Gold-Titanium Alloy*"; Published Mar. 11, 1997.
Internet Document: Fisher, J.; Abstract of: "*Ceramic Bonding To A Dental Gold-Titanium Alloy*"; Biomaterials; Mar. 2002, vol. 23, (5),pp. 1303-1311.
Internet Document: Matsuda, Fukuhisa, et al.; Abstract of: "*Surface Hardened Gold Alloys*"; Finishing, Sep. 1984, vol. 8, pp. 29-32.
Internet Documents(2): Fisher, J.; Abstract of: "*Effect of Small Additions of Ir on Properties of a Binary Au-Ti-Alloy*"; Dental Materials; Jun. 2002, vol. 18 (4), pp. 331-335.
Ott, Dieter; "*Effect of Small Additions and Impurities on Properties of Carat Golds*"; FEM Schwäbisch Gmünd, Germany; World Gold Council; 1997, pp. 31-37.
Ning, Yuantao; "*Alloying and Strenghtening of Gold Via Rare Earth Metal Additions*"; Kunming Institute of Precious Metals; Gold Bulletin , 2001, vol. 34 (3); pp. 77-87.
Poliero, Massimo; "*White Gold Alloys for Investment Casting*"; Leg.Or. s.r.l., Bressavido, Vicenza, Italy; pp. 10-20.
Grimwade, Mark; "*The 15th Santa Fe Symposium on Jewellery Manufacturing Technology*"; World Gold Council and the Worshipful Company of Goldsmiths, UK; pp. 18-19.
Patent Abstracts of Japan, Publication No. 56003636, Date of publication of application Jan. 14, 1981, in the name of Jiyousai Shika Daigaku.
Derwent Publications, Inc., Mosc Alloys Works XP-002343511, Database WPI, Jun. 25, 1977, 1 page, Section Ch, Week 197811, London, GB.
Derwent Publications, Inc., Sumitomo Metal Mining XP-002343512, Database WPI, Jul. 14, 1998, 1 page, Section Ch, Week 199838, London, GB.
Derwent Publications, Inc., Ishifuku Kinzoku Kogyo KK XP-002343513, Database WPI, Nov. 30, 1976, 1 page, Section Ch, Week 197703, London, GB.
Kempf, Bernd et al., Canadian Patent Application No. 2,170,084 filed Feb. 22, 1996 entitled Use of Gold Alloys for Precision Attachments in Dental Technology.
European Patent Search Report dated Sep. 5, 2005 for corresponding International Application No. EP 04 09 0367, in the name of The Argen Corporation, 5 pages.

* cited by examiner

Primary Examiner—Roy King
Assistant Examiner—Janelle Morillo
(74) Attorney, Agent, or Firm—Kauth, Pomeroy, Peck & Bailey LLP

(57) ABSTRACT

Dental prostheses are machined from a metallic body instead of being made by lost wax casting. Suitable gold base alloys have only base metal alloying additions which are more readily oxidized than gold and when combined with the gold can be age hardened. Exemplary metals include titanium, zirconium, yttrium and chromium. Scrap from the machining of a dental prosthesis is melted in air so that the base metals are all oxidized and substantially pure gold is reclaimed for reuse in new alloys.

8 Claims, No Drawings

DENTAL PROSTHESIS METHOD AND ALLOYS

FIELD OF THE INVENTION

This invention relates to preparation of dental restorations or prostheses incorporating gold alloys.

BACKGROUND

For over a century the ancient lost wax method of casting has been used to fabricate dental restorations. The success of this method is due to its simplicity, ease of use, and conservative nature of the process. Utilization of the precious metal used for restorations or prostheses of over 95% is easily obtained by remelting the sprues and button attached to the casting. In order to obtain less than 5% waste, the alloy cannot contain volatile elements or elements that are too readily fluxed into slag so that they are lost while the alloy is molten.

Over the last decade the technology of computer controlled machining or milling, CAD/CAM has increasingly been applied to the fabrication of dental prostheses, in particular those made from ceramics. For the dental laboratory the CAD/CAM process holds the promise of reducing labor expense while maintaining the laboratory's productivity.

The nature of the CAD/CAM operation requires the prosthesis to be milled from a larger body of material. The amount of material in the final product is usually a fraction of the amount of material in the original body. The amount of waste or scrap generated is often on the order of 80 to 90%. The process is cost effective for milling ceramics due to the low intrinsic cost of the ceramic materials. However, such a high proportion of waste is quite intolerable for precious metal alloys. For this reason, the milling process is rarely used for the fabrication of dental prostheses using precious metal. The problem is one primarily of economics. The nature of the CAD/CAM operation requires that the initial body of material be substantially greater than the finished part. Thus, the user must purchase more alloy than is necessary. While the amount of alloy may be minimized in some cases to reduce cost, the main economic factor is how to handle the waste or scrap from machining.

A few typical dental alloy compositions are shown in the following table.

| Au | 90 | 75 | 65 | 0 |
|---|---|---|---|---|
| Pt | 6 | 0 | 0 | 0 |
| Pd | 2 | 12 | 26 | 60 |
| Ag | 1 | 10 | 0 | 28 |
| In | .5 | 2 | 8 | 6 |
| Sn | 0 | 2 | 0 | 6 |
| Ir | 0.1 | 0.1 | 0 | 0 |
| Ru | 0 | 0 | 0.1 | 0.2 |
| Color | Yellow | White | White | White |

These alloys and others like them are all designed to be used for the lost wax method of casting. The alloying elements were chosen so that there is little loss of any particular component during the casting process. Using these alloys in a CAD/CAM milling operation however, would not be economical, since the large amount of scrap cannot be readily remelted into another body for re-use. The scrap material must be refined, that is, the scrap material must first be dissolved in acid and then each element retrieved separately. The refining process itself requires specialized equipment and the recovery of the platinum group elements in particular is quite expensive.

Such factors increase the final cost of the finished milled product, making it prohibitively expensive compared to the lost wax method of casting. This invention addresses the economic issue of recycling the waste products from milling by providing selected alloying additions to gold so that the gold can be readily recycled.

SUMMARY OF THE INVENTION

The present invention provides a process for forming a dental prosthesis from a metallic body comprising machining or milling a dental prosthesis from a metallic body comprising principally gold and at least one additional metal that in combination with the gold age hardens the alloy and is also more readily oxidized than gold. Afterwards, scrap resulting from machine milling the dental prosthesis is melted in an oxidizing environment to recover substantially pure gold.

Exemplary metals alloyed with the gold in a machined dental prosthesis include titanium, zirconium, yttrium and chromium. Barium or the like may also be included for grain refining.

DETAILED DESCRIPTION

Alloys suitable for practice of this invention consist essentially of gold and base metals, that is, metals that are more readily oxidized than gold. Thus, platinum group metals which do not readily oxidize are not included in the alloys. The principal base metal alloying ingredient or ingredients are those which age harden a gold alloy as well as being more readily oxidized than gold. The base metals are also biocompatible for use in the oral cavity. Examples are titanium, zirconium, yttrium and chromium.

If one considers a binary phase diagram of such an alloying element in gold, it is found that there is more solid solubility of the base metal in the gold at elevated temperatures and decreasing solubility with decreasing temperature. Commonly there are intermetallic compounds of the base metal and gold.

To age harden an alloy, it is maintained at a temperature higher than the line representing solid solubility until essentially all of the base metal is in solid solution in the gold. This does not necessarily require a reheating of the alloy, but may also occur upon cooling of the alloy from the molten state. The aging or age hardening occurs when the alloy is heated or maintained at a temperature below the solid solubility line so that the base metal segregates from a supersaturated solid solution and forms regions of intermetallic compound which interfere with deformation of the alloy, thereby increasing its hardness and strength. If the aging process is continued for a longer time (or at higher temperature), intermetallic compounds will precipitate from the alloy matrix, becoming non-coherent with the matrix crystal structure and the strengthening effect will be lost or degraded. Age hardening techniques are well known. Forming solid solutions and aging are kinetic phenomena, and the best times and temperatures for specific alloys are readily determined with only a few straightforward tests.

For example, a gold alloy with about 1.7% titanium has a solution heating cycle of about 15 minutes at 900 to 950° C. in air. If the alloy is used for a porcelain fused to a metal prosthesis, after applying the porcelain, the alloy is aged at 500° C. for about 15 minutes in air. It is believed that such a solution and aging cycle is also typical for other high-gold alloys of this invention.

Specific alloys found useful in the practice of this invention comprise principally gold with from 1 to 5% by weight of titanium, from 1 to 5% of zirconium, from 0.25 to 2% yttrium, or from 1 to 10% chromium. It is found that titanium and zirconium are effectively interchangeable on an atomic percentage basis. In other words, the hardening effect is similar for similar atomic percent content. Thus, ternary alloys of titanium and zirconium in gold may also be employed. Such an alloy would have from 0.5 to 4.5% titanium plus 0.5 to 4.5% zirconium with the total of titanium plus zirconium being in the range of from 1 to 5%. Other ternary alloys including base metals may also be employed. Percentages stated throughout the description and claims are all percent by weight.

Some examples of suitable alloys for practice of this invention are in the following table.

| Weight Percent | | | | Atomic Percent | | | As cast |
|---|---|---|---|---|---|---|---|
| Ti | Zr | Au | Alloy | Ti | Zr | Au | VHN |
| 0 | 1.5 | 98.5 | 1 | 0.0 | 3.2 | 96.8 | 67 |
| 0 | 2.5 | 97.5 | 2 | 0.0 | 5.2 | 94.8 | 174 |
| 0.5 | 0.5 | 99 | 3 | 2.0 | 1.1 | 96.9 | 79 |
| 0.5 | 1.5 | 98 | 4 | 2.0 | 3.1 | 94.9 | 188 |
| 1.5 | 0.5 | 98 | 5 | 5.9 | 1.0 | 93.1 | 206 |
| 1.5 | 2.5 | 96 | 6 | 5.7 | 5.0 | 89.2 | 236 |
| 1.5 | 0 | 98.5 | 7 | 5.9 | 0.0 | 94.1 | 123 |
| 2.5 | 0 | 97.5 | 8 | 9.5 | 0.0 | 90.5 | 240 |

Another example of a suitable alloy is 99.5% gold and 0.5% yttrium with an as cast VHN hardness of about 90. Pure gold has a VHN of about 30.

By modifying the nature and amount of base elements, high gold alloys with differing hardness and strength can be achieved. This allows the use of these alloys in a wide range of dental prosthetic applications.

Titanium, zirconium and yttrium are desirable additions since the alloy retains very nearly the color of pure gold. In this way the color of gold is preserved while strengthening the alloy. For the traditional dental alloys, the additions of palladium or platinum that are necessary to strengthen the alloy also whiten the alloy. In practice of this invention, when a white alloy is desired, chromium additions may be used. Chromium strengthens and whitens the alloy. Such gold chromium alloys are especially suited to machining since they are difficult to cold work.

Although the alloys consist essentially of gold and the base elements listed above, it can be desirable to include up to about 0.3% barium or some of the rare earth metals which act to refine grain size. Any such additions for grain refining are with metals more readily oxidized than gold. For example, iridium refines grain of high carat gold, but would not be useful since it is a platinum group metal that does not oxidize more readily than gold. Boron may also be useful although it would probably not be considered a metal and despite the fact that it has been found difficult to obtain consistent or reliable grain refining results.

The lower composition limits for the base metals mentioned above are the amounts of addition where a significant age hardening effect is seen. These limits are somewhat "fuzzy" or approximate, since the amount of age hardening desired may vary from one application to another. Furthermore, the lower limits may be lower when one uses a ternary alloy to obtain an equivalent age-hardening effect. It may also occur that there are other base metals which may be included in the alloy to form ternary intermetallic compounds, for example, which provide equivalent age-hardening. The upper limits of base metal concentration mentioned above are approximately the solid solubility limits of the respective metals in gold. These limits may differ somewhat in ternary alloys equivalent to the binary alloys.

A dental prosthesis or restoration may be made from such an age-hardenable alloy by machining. First, one makes a body of the alloy by conventional melting such as in a cold crucible arc furnace or in a heated crucible in a protective atmosphere. Or the alloy may be formed by levitation melting without contact with any crucible. Any conventional heating may be employed, including radiant heating and induction heating. Techniques for forming the body of alloy are all conventional.

The alloy is formed into a body that may be machined in the as-cast shape or a casting may be hot or cold worked, as desired, to a suitable geometry before machining. Machining may be of a body that is in the as-cast condition, hot worked, cold worked, annealed or age hardened.

Preferably, the body is machined to the geometry of the desired metal portion of the dental prosthesis by CAD/CAM since this is the least costly technique available. Any conventional machining may be used. The dental appliance or prosthesis made by machining may be entirely made of the alloy (i.e. with the bare metal showing), or may be a coping upon which dental porcelain is fired.

The alloys are particularly well suited for application of a porcelain layer since a thin adherent oxide film is readily formed from the base metals included in the composition. Porcelain may be applied after the prosthesis is age hardened and/or the age hardening may occur during the heating cycle for applying the porcelain coating. In the event there is age hardening before application of porcelain, care should be taken that the time and temperature of age hardening are low enough that the alloy does not over-age during application of the porcelain.

If desired, the alloy may be age hardened before machining and then solution treated so that it age hardens again during application of porcelain. The choice of these techniques are well within the skill of the art. Knowledge of the time and temperature cycle for applying porcelain to the dental prosthesis and the choice of porcelain which may be used, are not necessary for a practice of this invention. As a technician knows, mostly what is desired is a coefficient of thermal expansion compatible with that of the gold alloy. Of course, other properties of the porcelain such as hardness, color, and the like are also important for the technician in the dental lab, and those are well within the skill of the art.

During the course of machining a dental prosthesis from a body of alloy, an appreciable amount of scrap is produced as the larger body is machined to the desired geometry of the prosthesis. The scrap is accumulated, and it is not necessary to take any great care to keep different grades or compositions of scrap separated. Different compositions may be commingled since the base metals are essentially entirely removed upon subsequent processing of the scrap. The machining scrap should be segregated from scrap from lost wax casting since casting alloys commonly include platinum group metals that do not oxidize more readily than gold.

The scrap or chips from machining are melted in air or other oxidizing environment. Techniques such as induction heating are desirable to promote stirring of molten metal to expedite oxidation of the base metals in the alloy, but any heating technique is suitable.

For most rapid oxidation of the base metals a low melting metal oxide (including boron oxide, boric acid and metal borates which might not be considered metal oxides) and/or metal halide flux is melted on the surface of the scrap during this reclamation to combine with the base metal oxides. Powdered flux is mixed with accumulated machining scrap and when heated, the flux melts first, coating much of the metal scrap particle surfaces. The oxidative potential of such oxide fluxes is greater than air alone and expedites purification of the gold.

Cupellation could also be used for removal of base metal oxides but it is less efficient than melting with a flux and is best suited for rather small batches of metal. Cupellation may also be suitable for removing other base metals such as gallium, tin and/or indium which oxidize more readily than gold, but are not as readily removed in a flux as are the oxides of titanium, zirconium, yttrium and chromium.

An exemplary flux comprises a mixture of soda ash, borax (preferably anhydrous), silica and potassium nitrate. Other ingredients which may be used in fluxes include boric acid, boric oxide, sodium fluoride, potassium fluoride, sodium borate, potassium borate and miscellaneous silicates. The proportions may be varied to vary the oxidative potential of the flux. For example, increased oxygen compounds are preferred for expediting oxidation when the additional metal in the scrap is chromium, as compared with a lesser proportion of oxygen compounds which may be suitable when the additional metal is more readily oxidized than chromium, such as titanium, zirconium or yttrium.

The melting is continued for a sufficient time and at a sufficient temperature to substantially completely oxidize the base metals so that they are in the slag. The flux combines with the metal oxides produced and floats to the top of the molten gold as a liquid slag. After cooling, the brittle slag is removed and the remaining metal is substantially pure gold. "Substantially pure gold" does not mean that five-nines gold is produced, but that the purity of the gold remaining is commercially acceptable. Typically, this may be 99.5 to 99.9% gold. The gold thus refined can then be used in the same manner as any other refined gold.

Such scrap from machining a dental prosthesis may be remelted in the dental lab and/or may be traded or sold back to a vendor of dental alloys for reclamation. Likewise, a dental lab may purchase alloys and make bodies for machining from the alloy, or may purchase ready-made bodies or bars of alloy from which prostheses are machined without further processing at the lab.

It may be noted that some of the alloys mentioned above may be used in the conventional lost wax method for forming of dental prostheses. Publications have suggested a gold-titanium alloy for the lost wax casting method. It is not known that any of the other alloys used in the invention have been suggested for any method of making a dental prosthesis, either by lost wax casting or by machining.

What is claimed is:

1. A dental prosthesis formed of a gold based alloy consisting essentially of gold, and in weight %, from 0.5 to 2.5% titanium and in weight %, from 0.5 to 2.5% zirconium, the total of titanium and zirconium being in the range of from 1.5 to 3.0%.

2. The dental prosthesis according the claim 1 further comprising a grain refining metal that is more readily oxidized than gold and also refines the grain size of the gold alloy.

3. The dental prosthesis according the claim 1 further comprising up to 0.3wt % of an additional grain refiner selected from the group consisting of barium, boron and grain refining rare earth metal.

4. The dental prosthesis according to claim 1 wherein the alloy is has a gold content of greater than 90% by weight.

5. A body of dental gold based alloy for a dental prosthesis wherein the alloy consists essentially of gold, and in weight %, and from 0.5 to 2.5% titanium and in weight %, from 0.5 to 2.5% zirconium, the total of titanium and zirconium being in the range of from 1.5 to 3.0%.

6. The body of dental alloy for a dental prosthesis according to claim 5 wherein the alloy further comprises a grain refining metal that is more readily oxidized than gold and also refines the grain size of the gold alloy.

7. The body of dental gold based alloy for a dental prosthesis according the claim 5, the body further comprising up to 0.3 wt % of an additional grain refiner selected from the group consisting of barium, boron and grain refining rare earth metal.

8. The body of dental alloy for a dental prosthesis according to claim 5 wherein the body is formed of an alloy having a gold content of greater than 90% by weight.

* * * * *

UNITED STATES PATENT AND TRADEMARK OFFICE
CERTIFICATE OF CORRECTION

PATENT NO. : 7,279,054 B2 Page 1 of 1
APPLICATION NO. : 10/846314
DATED : October 9, 2007
INVENTOR(S) : Paul J. Cascone It is certified that error appears in the above-identified patent and that said Letters Patent is hereby corrected as shown below:

Col. 6, line 27, "is has a gold" should read -- has a gold --

Signed and Sealed this

Thirty-first Day of March, 2009

JOHN DOLL
*Acting Director of the United States Patent and Trademark Office*